United States Patent
Hochgraeber

(10) Patent No.: US 9,664,653 B2
(45) Date of Patent: May 30, 2017

(54) METHOD FOR FEEDING A SAMPLE INTO AN ANALYSIS BRANCH OF A LIQUID CHROMATOGRAPHY SYSTEM

(71) Applicant: DIONEX SOFTRON GMBH, Germering (DE)

(72) Inventor: Hermann Hochgraeber, Offenberg-Neuhausen (DE)

(73) Assignee: DIONEX SOFTRON GMBH, Germering (DE)

( * ) Notice: Subject to any disclaimer, the term of this patent is extended or adjusted under 35 U.S.C. 154(b) by 304 days.

(21) Appl. No.: 14/618,651

(22) Filed: Feb. 10, 2015

(65) Prior Publication Data
US 2015/0226710 A1    Aug. 13, 2015

(30) Foreign Application Priority Data
Feb. 10, 2014    (DE) .................. 10 2014 101 617

(51) Int. Cl.
*G01N 30/04*    (2006.01)
*G01N 30/16*    (2006.01)
*G01N 30/18*    (2006.01)
 G01N 30/24    (2006.01)
 G01N 30/02    (2006.01)

(52) U.S. Cl.
CPC ............. *G01N 30/16* (2013.01); *G01N 30/18* (2013.01); *G01N 30/24* (2013.01); *G01N 2030/027* (2013.01)

(58) Field of Classification Search
CPC ...................................................... G01N 30/04
USPC ........... 73/23.36, 23.41, 23.42, 61.56, 61.52, 73/61.55, 61.57; 96/101, 105
See application file for complete search history.

(56) References Cited

U.S. PATENT DOCUMENTS

| | | | |
|---|---|---|---|
| 3,615,234 A | 10/1971 | Ludvigsen | |
| 3,921,439 A * | 11/1975 | Burns | G01N 1/10 356/411 |
| 3,940,994 A * | 3/1976 | Klee | G01N 30/22 73/864.81 |
| 3,985,166 A | 10/1976 | Klee | |
| 4,618,935 A | 10/1986 | Schwartz | |

(Continued)

FOREIGN PATENT DOCUMENTS

| | | |
|---|---|---|
| CN | 101721839 A | 6/2010 |
| CN | 103487525 A | 1/2014 |

(Continued)

*Primary Examiner* — Michael A Lyons
*Assistant Examiner* — Hoang Nguyen
(74) *Attorney, Agent, or Firm* — Timothy J. Ohara

(57) ABSTRACT

The invention relates to a method for feeding a sample into an analysis branch of a liquid chromatography system, in particular a high-performance liquid chromatography system. A solvent or a solvent mixture from at least one solvent branch is supplied as volume flow $\dot{A}$ into the analysis branch. At least one sample from at least one sample branch is fed as volume flow $\dot{E}$ into the analysis branch within a predetermined time interval. The volume flow $\dot{A}$ is reduced to an extent during the predetermined time interval, and a volume flow $\dot{C}$ resulting from the sum of the volume flows $\dot{A}$ and $\dot{E}$ remains substantially constant in the analysis branch. The invention further relates to a sampler for carrying out a method of this kind.

10 Claims, 2 Drawing Sheets

(56) References Cited

U.S. PATENT DOCUMENTS

| | | | |
|---|---|---|---|
| 6,129,840 A | 10/2000 | Kitaoka | |
| 7,189,320 B2* | 3/2007 | Takao | F04B 9/02 210/101 |
| 7,624,626 B2* | 12/2009 | Lee | G01N 30/62 210/101 |
| 7,670,480 B2* | 3/2010 | Witt | G01N 30/32 137/7 |
| 8,515,587 B2* | 8/2013 | Witt | G01N 30/8658 700/266 |
| 8,748,191 B2* | 6/2014 | Kraus | G01N 35/1095 422/501 |
| 8,806,922 B2* | 8/2014 | Hochgraeber | G01N 30/20 73/61.55 |
| 2006/0144126 A1* | 7/2006 | O'Brien | G01N 1/2202 73/23.42 |
| 2009/0076631 A1 | 3/2009 | Witt et al. | |
| 2010/0037919 A1 | 2/2010 | Doebelin et al. | |
| 2010/0252502 A1* | 10/2010 | Witt | F04B 11/0058 210/656 |
| 2013/0206656 A1 | 8/2013 | Johl et al. | |

FOREIGN PATENT DOCUMENTS

| | | |
|---|---|---|
| DE | 1926672 | 12/1969 |
| DE | 102008006266 | 8/2009 |
| DE | 102009029028 | 5/2010 |
| DE | 102010034585 | 4/2012 |

* cited by examiner

METHOD FOR FEEDING A SAMPLE INTO AN ANALYSIS BRANCH OF A LIQUID CHROMATOGRAPHY SYSTEM

CROSS REFERENCE TO RELATED APPLICATIONS

This application claims the priority benefit under 35 U.S.C. §119 to German Patent Application No. 10 2014 101 617.3 by Hermann Hochgraeber for "METHOD FOR FEEDING A SAMPLE INTO AN ANALYSIS BRANCH OF A LIQUID CHROMATOGRAPHY SYSTEM, IN PARTICULAR A HIGH-PERFORMANCE LIQUID CHROMATOGRAPHY SYSTEM" filed on Feb. 10, 2014, the disclosure of which is incorporated herein by reference.

FIELD OF THE INVENTION

The invention relates to the injection of a sample and concerns the field of liquid chromatography, in particular high-performance liquid chromatography (HPLC).

BACKGROUND

In HPLC, a sample that is stored at atmospheric pressure is generally conveyed with the aid of a metering pump, in an automated method (autosampler), into a sample loop which is connected at both ends to what is called a shear valve. When the desired amount of the sample is located in the loop, the shear valve is switched such that the solvent stream now flows through the sample loop, and the sample can thus be conveyed at high pressure through the separating column. This procedure by which the sample to be analyzed is fed or introduced into the solvent stream is called (sample) injection.

However, particularly at high operating pressures of a chromatography system, shear valves can be switched only with high drive moments. The rubbing and sealing shear surfaces are therefore subject to a high degree of wear and have to be frequently replaced. Despite the high sealing normal force, the positioning of the two shear surfaces relative to each other also requires a high level of precision. The shear surfaces are also very sensitive to abrasive constituents in the solvent stream or sample stream. Upon switching of the shear valves, the flow or the volume flow through the column is interrupted for the switching time, such that the pressure upstream of the separating column drops and the pressure in the high-pressure pump rises. In particular, the pressure drops particularly strongly when the sample loop, at atmospheric pressure after suction of the sample, is introduced into the feed line to the column, and the high-pressure pump has to compress the content of the sample loop to the operating pressure upstream of the column. During this time, the direction of flow in the feed line to the separating column reverses, which reduces the useful life of the separating column and has a negative effect on the separation efficiency.

DE 10 2008 006 266 B4 has already disclosed an arrangement which, with the aid of a shear valve, is able to completely eliminate the fluctuations in pressure that occur during injection according to the prior art.

However, manual injections of samples, of the kind described in the patent documents U.S. Pat. No. 3,985,166 and U.S. Pat. No. 3,940,994 for example, are unsuitable for an automated method in what is called an autosampler, with different samples having to be collected from several vials or several sample reservoirs. Moreover, during such an injection, the sample is diluted in the solvent stream, which results in poor sample detection.

SUMMARY

Therefore, the object of the present invention is to make available a method for feeding a sample into an analysis branch to a separating column in liquid chromatography, in particular in high-performance liquid chromatography, and also an automatic sampler, which method and sampler reduce wear, error susceptibility and maintenance in a simple and cost-effective manner and yet still permit high quality of the sample detection.

According to the invention, the volume flow $\dot{C}$ in an analysis branch to a separating column is kept constant. The analysis branch (possibly also divided into several subsidiary branches with several separating columns) is connected here to (at least) one solvent branch and (at least) one sample branch, such that the volume flow $\dot{C}$ results from a sum of a volume flow $\dot{A}$ in the at least one solvent branch and of a volume flow $\dot{E}$ in the at least one sample branch. However, the injection of a sample from the at least one sample branch does not take place by switching a complicated shear valve with several ports, but instead by reducing the volume flow $\dot{A}$ in the at least one solvent branch, such that a volume flow $\dot{E}$ of greater than zero exists during the injection time. Such reduction/increase can preferably be obtained by corresponding control (switching off or reducing the power consumption or switching on or increasing the power consumption) of a pump responsible for this branch. However, it is of course also conceivable for the reduction of the volume flow $\dot{A}$ in the solvent branch to be brought about by means of a suitably controllable valve.

By reducing the volume flow $\dot{A}$ in the at least one solvent branch (possibly divided into several subsidiary branches), it is possible for a sample from a sample branch to be supplied as volume flow $\dot{E}$ to the analysis branch, without a change in the volume flow $\dot{C}$ taking place. The injection of the at least one sample or of the at least one sample plug as a result of the volume flow $\dot{E}$ (equals zero before injection of the sample) can already take place through a simple Y connection with two inputs (solvent branch and sample branch) and one output (analysis branch). Only a reduction of the volume flow $\dot{A}$ causes the volume flow $\dot{E}$ to increase (from zero) to a corresponding extent. For this purpose, for example, a (metering device) pump, or the drive thereof, responsible for the at least one sample branch can be controlled (started up or its power consumption increased). In this way, the at least one sample can advantageously be introduced into the solvent stream to the separating column (analysis branch) without the complicated drive and the wear of a shear valve. Moreover, the method according to the invention and the arrangement for carrying out said method ensure that, when the sample is introduced into the analysis branch, the flow (volume flow) does not change either in direction or in quantity.

It is assumed here that a flow running counter to the pump direction (reverse flow), for example design-related or caused by a unidirectional valve, is suppressed by the corresponding pumps, either controllably (for example a solenoid valve) or preferably by self-regulation (in particular a check valve). The pumps can be controlled via a control device or regulator connected correspondingly to the drives of the pumps. In addition, for monitoring purposes, pressure sensors can be provided in the solvent branch and/or in the sample branch, which pressure sensors transmit the detected parameters in each case to the control device or regulator.

In a preferred embodiment, a unidirectional valve with 2 switching positions, in particular a closed position and an opened position, is additionally located in the sample branch (possibly divided into several subsidiary branches), in particular upstream of the sample, seen in the direction of flow, so as to be able to use the (respective) sample plug with particular accuracy. Instead of being designed as a valve controllable by a motor, such a valve can also be designed for example as a pressure-dependent valve, in particular a simple check valve. In this way, intermixing effects can advantageously be prevented at the front of the sample, and an exactly defined front separation surface between sample (plug) and solvent can be achieved. Moreover, with such a valve, the sample branch can also be disconnected if need be, such that an opening of the sample branch and the associated drop in pressure has no effect on the solvent branch and/or the analysis branch. Correspondingly, in the at least one sample branch, under other pressure conditions (than the high system pressure prevailing in the solvent branch and/or analysis branch), in particular the ambient pressure, another sample reservoir can be inserted or connected hereto (as is explained below, for example, with an injection needle being pressed into a needle seat). In this way, the longitudinal intermixing of the injected sample with the solvent on the way to the separating column can be advantageously minimized.

In a further embodiment of the invention, the volume flow $\dot{A}$ comes to a complete standstill after a possible transition phase during a predefined time interval for the (sample) injection. The solvent pump can also be stopped and the metering device pump can also be started (instead of a reduction or increase in power consumption). The volume flow $\dot{C}$ resulting from the sum of the volume flows $\dot{A}$ and $\dot{E}$ then corresponds after a very short transition time (in the millisecond range or ≤one millisecond) to the volume flow $\dot{E}$, such that a dilution of the sample or of the sample plug can be avoided. Before and after the sample injection, the volume flow $\dot{C}$ corresponds by contrast to the volume flow $\dot{E}$, such that the constant maximum of the volume flow $\dot{C}$ is formed either by an, at the respective time, constant maximum of the volume flow $\dot{A}$ or $\dot{E}$.

In a particularly preferred embodiment of the invention, the volume flow $\dot{E}$ (in particular for feeding the sample in from a sample loop) is stopped before a rear end, seen in the direction of flow, of the sample or transition between sample end and solvent (in the sample branch) reaches the analysis branch. In this way, a (new) rear transition with exactly defined separation surface is obtained on the sample used in the volume flow $\dot{C}$, compared to the transition already existing in the sample branch in previously used methods. Intermixing effects caused by the movements needed during the collection and release of a sample are advantageously avoided.

In a further embodiment of the invention, after a sample has been collected, an injection needle for injecting the sample is pressed with a high degree of sealing (high degree of sealing in relation to the pressures customary in HPLC) into a needle seat, which is connected to the analysis branch, preferably via a valve, in particular a check valve. The injection needle can in this case not only remove samples in an automated manner from vials (i.e. different reservoirs) under motor control, preferably maintaining its vertical position, but can also be pressed sealingly into the needle seat in an automated manner. This can permit not only semi-automatic but even completely automated sample injection, including sample removal from different vials or reservoirs. Moreover, the dispensing of a defined amount of sample is also facilitated by a valve of this kind (in particular closing in one direction), since the sample branch is closed, or sealingly disconnected from the analysis branch and/or solvent branch, after the desired amount of sample has been dispensed.

In a further embodiment of the invention, after the sample has been used, the injection needle is automatically cleaned by flushing before a further sample is collected. The flow off can take place, for example, via what is called a waste port (collector, optionally with a drain additionally provided). In this way, it is possible to avoid undesired contamination of the (next) sample. In particular, in order to permit multiple sampling while avoiding gassing, the injection needle can be connected to what is called a sample loop which, prior to the sampling, contains a sample with solvent.

Moreover, it is also conceivable to clean or flush the sample loop and metering device by introduction of solvent. For this purpose, for example, solvent can be introduced via the needle or via another attachment of the metering device, in particular by means of a flushing pump, and can be discharged via the other attachment or the needle or additional (waste) port of the metering device.

In a further embodiment of the invention, solvent or a solvent mixture can be fed into the analysis branch after or before a sample injection by means of the metering device and/or an additional pump (for example flushing pump). In this way, for example, the analysis branch (including the column) can be flushed or cleaned. Moreover, it is also conceivable in this way, for example by injection of a solvent fraction, to form the gradient in a desired manner (in particular in the direction of a higher elution).

According to the invention, as a result of the constant volume flow in the analysis branch (not only during a sample run but in particular during a sample injection), it is advantageously possible to ensure a desired, distinct separation (in particular exact separation surfaces) between sample or sample plug and solvent, both at the front and also at the rear as seen in the direction of flow.

By contrast, the effects of intermixing (diffusion, etc.), which occur at the separation surfaces on account of fluctuations in volume flow in the analysis branch, for example in sample injection in U.S. Pat. No. 3,940,994, can advantageously be reduced or even avoided, and the analysis precision can be greatly increased.

BRIEF DESCRIPTION OF THE DRAWINGS

The invention is explained in more detail below on the basis of an illustrative embodiment depicted in the drawings.

DETAILED DESCRIPTION OF EMBODIMENTS

Figure 1:
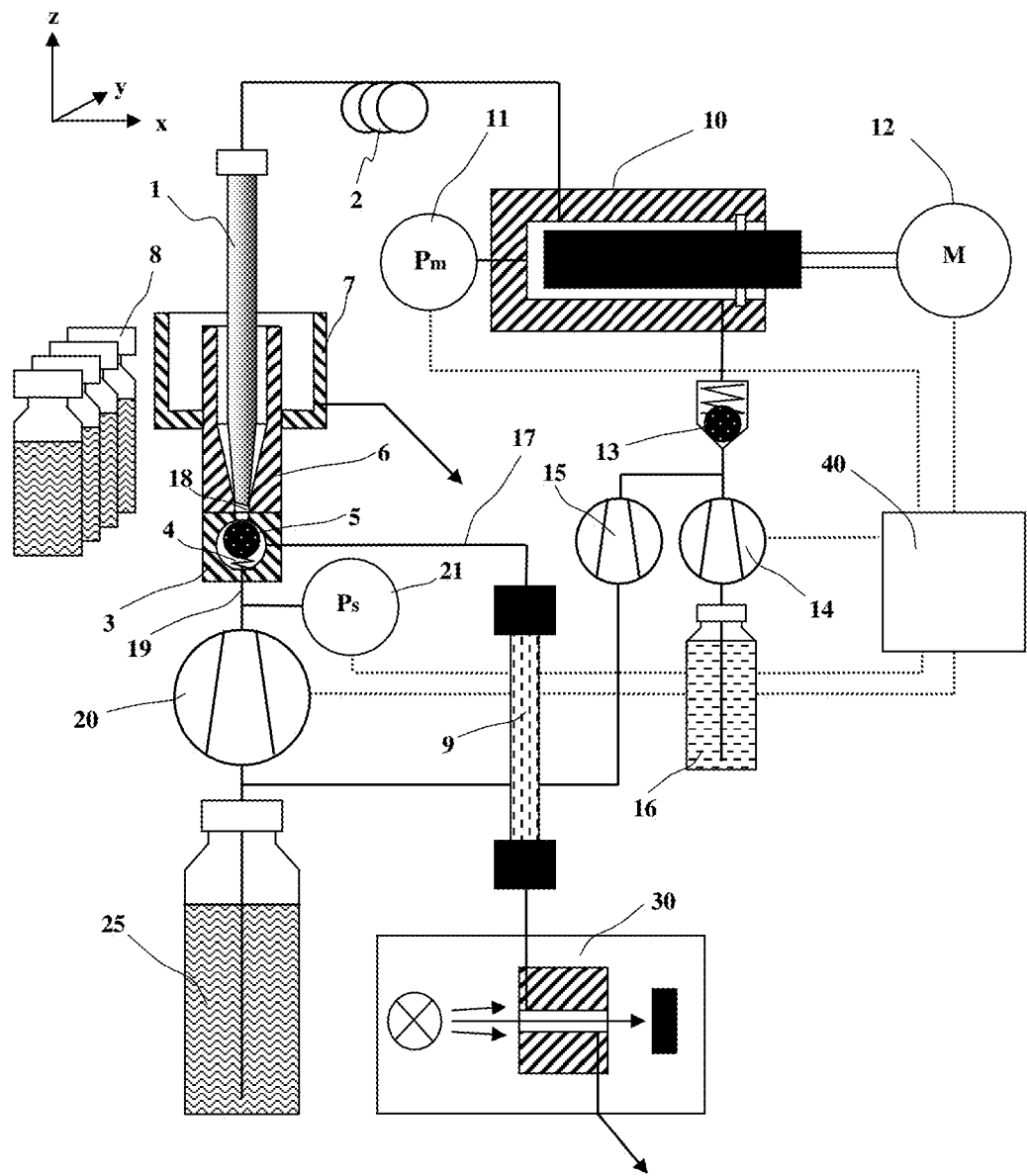
FIG. 1 shows a schematic view of a sampler according to the invention.

The arrangement in FIG. 1 shows an automatic sampler, or autosampler, and its integration into a chromatography system. The autosampler comprises an injection needle 1 which, in a manner not shown in detail in the drawing, can be moved under the control of a motor in the x-y-z direction (x horizontal, z vertical in the plane of the drawing, and y perpendicular to the plane of the drawing), and also a sample loop connected thereto, and a metering device 10.

By way of the injection needle 1, a sample from a vial 8 is drawn into a sample loop 2 by means of the metering device 10 (for example, as shown in the drawing, in the form of a piston pump). Thereafter, the injection needle 1 is pressed sealingly into a needle seat 6, to which a check valve 3 is attached. In normal operation, a solvent or mobile phase is aspirated (solvent branch 19) via a pump 20 (HPLC pump) and is guided via the check valve 3 to the column 9 (analysis branch 17). In this state, the port on the valve leading to the needle seat 6 is closed by a closure means, for example a ball 5, optionally pretensioned by a restoring element, for example a spring 4.

If the sample is now to be fed in or introduced, the pressure that the metering device 10 has to apply must be greater than the prevailing system pressure, so that the check valve 3 opens. Moreover, the solvent pump 20 has to stop its flow during the sample injection time, so as to prevent a pressure increase in the connected solvent branch 19 and analysis branch 17.

The sample is now pumped by the metering device 10 out of the sample branch 18 (content of the pressed-in needle 1 as far as the connected port of the check valve 3) in the direction of the column 9. After a desired amount of the sample located in the needle 1 has been fed in and the metering device 10 has stopped the supply, the check valve 3 closes automatically and the solvent pump 20 starts supplying again.

In order to avoid increases or decreases in flow (volume flow $\dot{C}$ in the analysis branch) and in pressure in this injection process, data communication takes place (for example by means of a control device 40) between autosampler (metering device 10, sample loop 2 and needle 1) and solvent pump 20, which data communication coordinates the flow responsibility between metering device 10 and solvent pump 20.

In this way, a desired and definable amount of a sample is fed directly into the solvent stream to the separating column 9, without the sample being diluted with the solvent stream. Moreover, the low sample dispersion and the low longitudinal intermixing not only increase the precision of the analysis (in the schematically depicted detector 30) but also prolong the useful life of the column 9.

As can be seen from FIG. 1, the sample loop 2 and injection needle can be flushed and cleaned via the metering device 10 by means of a flushing pump 14, which is connected to a flushing agent reservoir 16, after which the sample loop 2 and the inside of the needle 1 are filled by means of pump 15 which, like the pump 20, is also connected to a reservoir for the solvent 25 (fluid). Of course, it is also conceivable to use the solvent 25 also for cleaning purposes, in which case the additional pump 14 and flushing agent 16 can be dispensed with. The sample loop is filled with solvent all the way to the tip of the injection needle 1, in order to avoid gassing of a sample generally degassed in HPLC and to avoid undesired mixing of the sample. To hold the corresponding solvent column in the autosampler, it is possible, as shown schematically in the drawing, to provide a corresponding check valve 13, in order to prevent reverse flow and also forward ejection from the needle 1.

Since the needle 1 is sterile before use and is contaminated during a sampling procedure in which a septum of a vial 8 is usually pierced, an aforementioned cleaning procedure according to the invention takes place after an injection of sample but before a renewed collection of sample, such that a sterile state is ensured once again after such cleaning.

As is shown schematically in FIG. 1 by the four vials 8, it is possible according to the invention to collect samples successively from several different vials 8 (as is customary in HPLC) and then inject them. The vials 8 can be arranged in an autosampler, for example in the form of a tray or a (micro)titer plate (well plates).

To permit flushing directly after the injection of a sample, the needle seat 6 has, on its upper face, an overflow container 7 which extends around the needle seat and is open toward the top, such that any emerging flushing liquid and/or solvent can collect in this overflow container and can flow off and be discarded as indicated by the bent arrow. In this way, a large number of samples can be collected and injected using the sampler according to the injection, wherein the flushing after the injection and before renewed collection of a sample prevents contamination of the subsequent sample and therefore of the next sample run.

To control the aforementioned procedures and, in particular, to keep the volume flow in the analysis branch 17 constant, it is possible for the pump 20 and the metering device 10, and the drive motor 12 thereof, to be suitably controlled via the control device. By contrast, the corresponding control of the pumps 14 and/or 15 takes place exclusively, as has been explained above, for cleaning purposes and for keeping solvent in the sampler. To permit a particularly high level of precision of the control, it is possible, as is shown schematically in FIG. 1, to additionally provide a pressure sensor 21 in the solvent branch 19 and a pressure sensor 11 in the sample branch 18, said pressure sensors transmitting actual states to the control device, which actual states are evaluated there. Pressure sensors 21 and 11 of this kind can also be integrated in the pump 20 and the metering device 10.

Figure 2:
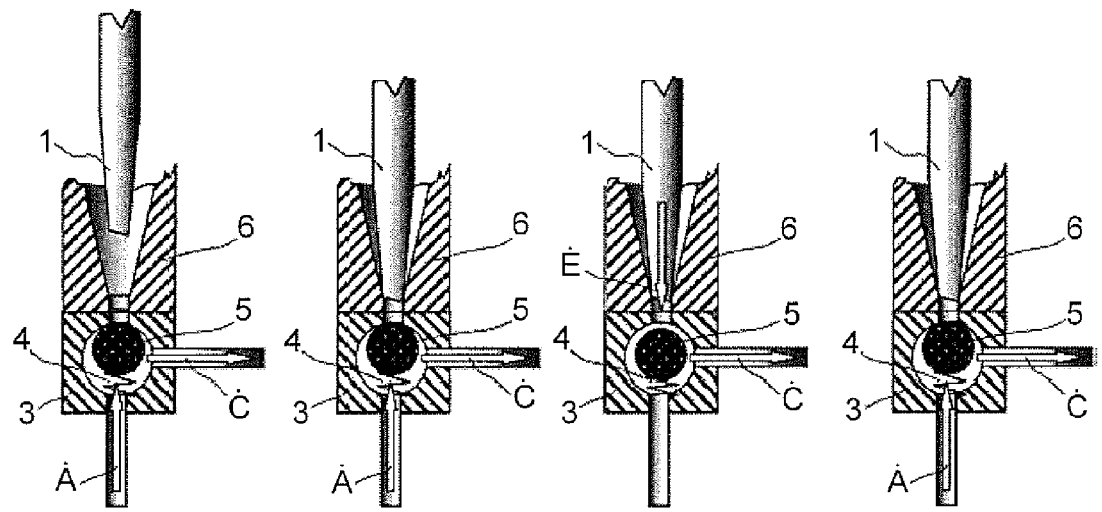
FIG. 2 shows a schematic view of a detail from FIG. 1.

The enlarged detail of the needle seat 6 in four positions in FIG. 2 shows how, in a first position, the valve 3 in the blocked state closes the port to the needle seat 6 by means of ball 5, and the volume flow $\dot{C}$ thus corresponds to the volume flow $\dot{A}$. In this valve position, the needle 1 can still be located outside the needle seat 6, without solvent emerging through the closed port of the check valve to the needle seat. Thereafter, the needle tip 1 is pressed sealingly into the needle seat 6 (as is shown in the second partial figure from the left in FIG. 2), such that the port of the valve 3 to the needle seat 6 is sealingly closed and, in this position, the port is also closed by the ball 5.

The third partial figure in FIG. 2 shows how the volume flow $\dot{A}$ has already been stopped, the ball 5 comes loose, upon pressure equality with the pressure present in the system or solvent branch 19 and the analysis branch 17 connected thereto, and frees the port to the needle seat, and the sample is injected into the analysis branch 17 through the volume flow $\dot{E}$. The view on the right in FIG. 2 shows once again how the sample injection has been stopped preferably after introduction of a predefined amount of volume flow $\dot{E}$, smaller than the amount of sample contained in the needle 1 and sample loop 2, and the volume flow $\dot{C}$ is once again fed in from the volume flow $\dot{A}$ of the solvent. Although, in a preferred embodiment of the method, not all of the sample amount contained in the sample loop 2 and needle 1 is fed into the volume flow $\dot{C}$, and part of the contained sample is thereby lost, this method can be advantageous since in this way intermixing effects at the rear separation surface can be avoided. Such intermixing effects otherwise occur, since the rear separation surface has been moved rearward in the sampling procedure and been moved forward again during the sample injection, until it is present as separation surface in the volume flow $\dot{C}$. However, through these movements, the separation surface is unclear because of intermixing effects, and this has a disadvantageous effect on the accuracy of the analysis in the detector 30.

Figure 3:
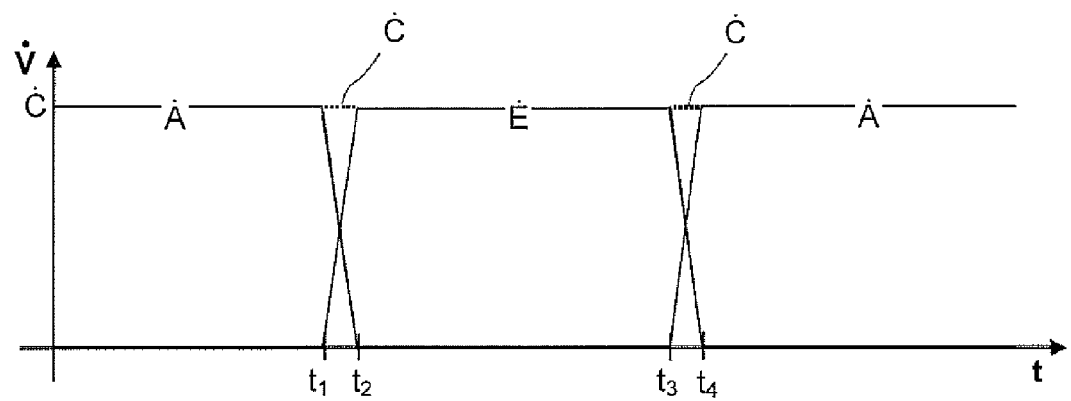
FIG. 3 shows a diagram of the volume flows in a sampler according to FIG. 1.

The diagram of volume flow per time in FIG. 3 shows how a volume flow $\dot{C}$ is composed as resultant of the sum of volume flows $\dot{A}$ and $\dot{E}$. In valve position closed (partial figures on the left, second from the left, and on the right in FIG. 2), the volume flow $\dot{A}$ is constant and continues as constant volume flow $\dot{C}$. A volume flow $\dot{E}$ does not exist at this time (before T1 and after T4).

In the opened position, as shown in the third view from the left in FIG. 2, the volume flow $\dot{A}$ has been stopped by stopping the pump 20, such that in the area between T2 and T3 the volume flow $\dot{E}$ continues to the volume flow $\dot{C}$. In the transition phases T1-T2 and T3-T4 which, compared to the sample injection duration of for example 10 ms to 1 min, are short (for example 1 ms or less, but at least under a few ms), the volume flow $\dot{E}$ rises (or falls) to the extent that the volume flow $\dot{A}$ falls (or rises). Although the respective flanks are shown schematically in FIG. 3 as straight lines, the corresponding rise and fall can of course also take place according to suitable curves. In a preferred embodiment of the invention, however, suitable control of the pump 20 and of the metering device 10, even during opening of the valve 3 in the transition phase T1-T2 and during closure of the valve 3 in the transition phase T3-T4, ensures that at each time the sum of the volume flows reaches the same level as the preceding volume flow $\dot{A}$ and the succeeding volume flow $\dot{E}$ (transition closed to open) or the preceding volume flow $\dot{E}$ and the succeeding volume flow $\dot{A}$ (at the transition open to closed). By maintaining a constant volume flow not only before, during and after an injection of sample but also in the transitions (T1-T2 and T3-T4), a sample or a sample plug is fed in while maintaining clear separation surfaces, and, as has already been explained above, it is possible to prevent reverse intermixing, seen in the direction of flow, on account of movements in needle 1 and sample loop 2 by a separation of a predefined amount of sample from the entire contained sample.

As is customary in HPLC, a sample run takes place at very high pressure, for example in excess of 500 bar or even in excess of 1000 bar, such that, with the required narrow cross sections in the analysis branch (10 μm-max. 1 mm), it is possible to generate volume flows of several μl-10 ml per minute, preferably under 100 ml per minute, in particular under 300 μl per minute, but at the respectively desired level with a constancy of a deviation of under 25%, for example under 10% or under 5%, in particular ≤1%, in order to protect the separating column from disadvantageous and excessively high fluctuations in flow. A whole sample run can in this way last from a few minutes or so to one hour, until the substance and sample pass through the column 9 to the detector 30.

LIST OF REFERENCE SIGNS 1 injection needle
2 sample loop
3 check valve
4 spring
5 ball
6 needle seat
7 overflow container
8 vials
9 separating column
10 metering device (piston pump)
11 pressure sensor
12 drive for metering device 10
13 check valve
14 flushing pump
15 flushing pump
16 flushing agent
17 analysis branch
18 sample branch
19 solvent branch
20 HPLC pump
21 pressure sensor
25 solvent (fluid)
30 detector
40 control device
$\dot{A}$ volume flow for supplying solvent 25 from a solvent branch
$\dot{E}$ volume flow for feeding the sample from the sample branch into the analysis branch
$\dot{C}$ volume flow in the analysis branch to the separating column 9, which volume flow results from the sum of volume flows $\dot{A}$ and $\dot{E}$

What is claimed is:

1. A method for feeding a sample into an analysis branch of a liquid chromatography system, the method comprising:
   supplying a solvent or a solvent mixture from at least one solvent branch at a volume flow $\dot{A}$ into the analysis branch, the at least one solvent branch is an input into a unidirectional valve, the analysis branch is an output out of the unidirectional valve;
   feeding at least one sample from at least one sample branch at a volume flow $\dot{E}$ into the analysis branch within a predetermined time interval, the at least one sample branch is another input into the unidirectional valve
   reducing the volume flow $\dot{A}$ during the predetermined time interval, in which the reducing of the volume flow $\dot{A}$ causes an increase in the volume flow $\dot{E}$, and a control device controls the volume flow $\dot{A}$ and the volume flow $\dot{E}$;
   outputting a substantially constant volume flow $\dot{C}$ in the analysis branch resulting from a sum of the volume flows $\dot{A}$ and $\dot{E}$.

2. The method of claim 1, wherein the volume flow $\dot{A}$ comes to a stop during the predetermined time interval
   at least after introducing the sample into the analysis branch where a solvent pump is stopped and a metering device pump is started, the solvent pump being configured to pump the solvent into the solvent branch, the metering device pump being configured to pump the sample into the sample branch.

3. The method of claim 2, wherein the volume flow $\dot{A}$ comes to a stop during the predetermined time interval,
   at least after a first transition phase where the sample is introduced into the analysis branch, the solvent pump is stopped, and the metering device pump is started, and
   at least before a second transition phase where the sample has already been introduced into the analysis branch, the solvent pump is started, and the metering device pump is stopped.

4. The method of claim 1, wherein the volume flow $\dot{C}$ corresponds to a maximum of the volume flow $\dot{A}$ or $\dot{E}$.

5. The method of claim 3 further comprising:
   stopping the volume flow $\dot{E}$ of the sample into the unidirectional valve before a first rear end of the sample, with respect to a direction of a flow of the sample, reaches the analysis branch, the rear end being a transition between an end of the sample and the solvent, whereby a second rear end arises on the sample introduced into the volume flow $\dot{C}$ of the analysis branch.

6. The method of claim 1 further comprising:
collecting the sample from a vial; and
after collecting the sample from the vial, pressing an injection needle into a needle seat to introduce the sample to the sample branch, in which the needle seat is connected to the analysis branch via the unidirectional valve.

7. The method of claim 6 further comprising: after introducing the sample to the sample branch and prior to collecting a further sample, automatically cleaning the injection needle by flushing.

8. The method of claim 1, wherein the supplying of the solvent or the solvent mixture into the analysis branch is after or before the feeding of the at least one sample.

9. The method of claim 2, in which the supplying of the solvent or the solvent mixture to the at least one solvent branch causes a ball in the unidirectional valve to close the sample branch.

10. The method of claim 9, in which the solvent pump is stopped and causes the ball to open the sample branch allowing the sample to feed into the analysis branch.

\* \* \* \* \*